US00PP24331P2

(12) United States Plant Patent
Dixon

(10) Patent No.: US PP24,331 P2
(45) Date of Patent: Mar. 18, 2014

(54) ***GAILLARDIA* PLANT NAMED 'MOXIE'**

(50) Latin Name: *Gaillardia×grandiflora*
Varietal Denomination: Moxie

(76) Inventor: John Armand Dixon, Mound Vernon, WA (US)

( * ) Notice: Subject to any disclaimer, the term of this patent is extended or adjusted under 35 U.S.C. 154(b) by 118 days.

(21) Appl. No.: 13/507,071

(22) Filed: May 30, 2012

Related U.S. Application Data

(60) Provisional application No. 61/519,888, filed on Jun. 1, 2011.

(51) Int. Cl.
*A01H 5/00* (2006.01)

(52) U.S. Cl.
USPC ..... Plt./431

(58) Field of Classification Search
USPC ..... Plt./431
See application file for complete search history.

(56) References Cited

U.S. PATENT DOCUMENTS

| | | | | |
|---|---|---|---|---|
| PP15,892 | P2 * | 7/2005 | Read | Plt./431 |
| PP19,943 | P2 * | 4/2009 | Dixon | Plt./431 |
| PP19,944 | P2 * | 4/2009 | Dixon | Plt./431 |

* cited by examiner

*Primary Examiner* — Wendy C Haas
(74) *Attorney, Agent, or Firm* — Penny J. Aguirre

(57) ABSTRACT

A new cultivar of *Gaillardia*, 'Moxie', characterized by its semi-compact plant habit and its inflorescences with ray florets that are fluted and yellow in color with orange highlight in the eye zone (base) and disk florets that are orange in color.

2 Drawing Sheets

Botanical classification: *Gaillardia×grandiflora*.
Variety denomination: 'Moxie'.

CROSS REFERENCE TO A RELATED APPLICATION

This application is related to U.S. Plant Patent for plants from the same breeding program entitled Gaillardia Plant Named 'Frenzy' (U. S. Plant Pat. No. 19.944) and Gaillardia Plant Named 'Tizzy' (U.S. Plant Pat. No. 19,943).

BACKGROUND OF THE INVENTION

The present invention relates to a new and distinct cultivar of *Gaillardia* plant, botanically known as *Gaillardia×grandiflora* 'Moxie' and will be referred to hereinafter by its cultivar name, 'Moxie'.

'Moxie' was derived from a controlled breeding program conducted by the Inventor in LaConner, Wash. The breeding program focuses on obtaining new cultivars of *Gaillardia* with fluted ray florets. 'Moxie' arose from a cross made in June 2008 between *Gaillardia×grandiflora* 'Frenzy' as the female parent and an unnamed plant of *Gaillardia grandiflora* from the inventor's breeding program as the male parent. 'Moxie' was selected in August 2009 as a single unique plant from the resulting seedlings.

Asexual reproduction of the new cultivar was first accomplished via stem cuttings by the inventor in LaConner, Wash. in October 2009. The characteristics of this cultivar have been determined to be stable and are reproduced true to type in successive generations.

SUMMARY OF THE INVENTION

The following traits have been repeatedly observed and are determined to be the characteristics of the new cultivar of

*Gaillardia*. These attributes in combination distinguish 'Moxie' as unique from all other varieties of Gaillardia known to the Inventor.

1. 'Moxie' exhibits inflorescences with ray florets that are fluted and yellow in color with orange highlight in the eye zone (base) and disk florets that are orange in color.
2. 'Moxie' exhibits a semi-compact plant habit.
3. 'Moxie' blooms earlier in the season than the male parent.
4. 'Moxie' blooms later in the season than its female parent.

'Frenzy', the female parent, differs from 'Moxie' in having ray florets that are longer, red to orange in color, in being less vigorous, in being more difficult to propagate, and in blooming earlier. The male parent differs from 'Moxie' in having ray florets that are not fluted and lack orange highlights in the eye zone, in having a less compact plant habit, and in blooming later. 'Moxie' can also be compared to *Gaillardia* cultivars 'Fanfare' (U.S. Plant Pat. No. 15,892) and 'Tizzy' (U.S. Plant Pat. No. 19,944). 'Fanfare' differs from 'Moxie' in having ray florets that are yellow-orange in color with red highlights. 'Tizzy' differs from 'Moxie' in having ray florets that are red in color.

BRIEF DESCRIPTION OF THE DRAWINGS

The accompanying colored photographs illustrate the overall appearance and distinct characteristics of the new *Gaillardia*. The photographs were taken of a plant two years in age as grown outdoors in a 3-gallon container in LaConner, Wash.

The photograph in FIG. 1 provides a view of a 'Moxie' in bloom (center plant in a mixed container).

Figure 1:
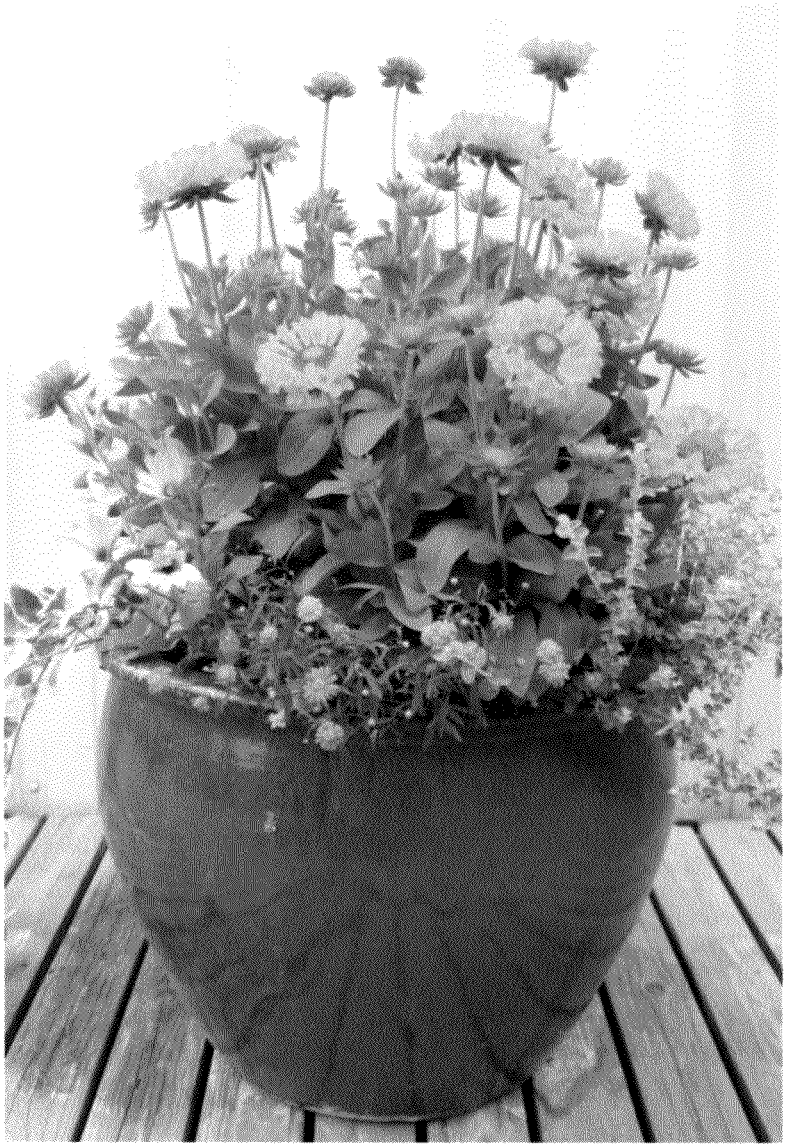
Figure 2:
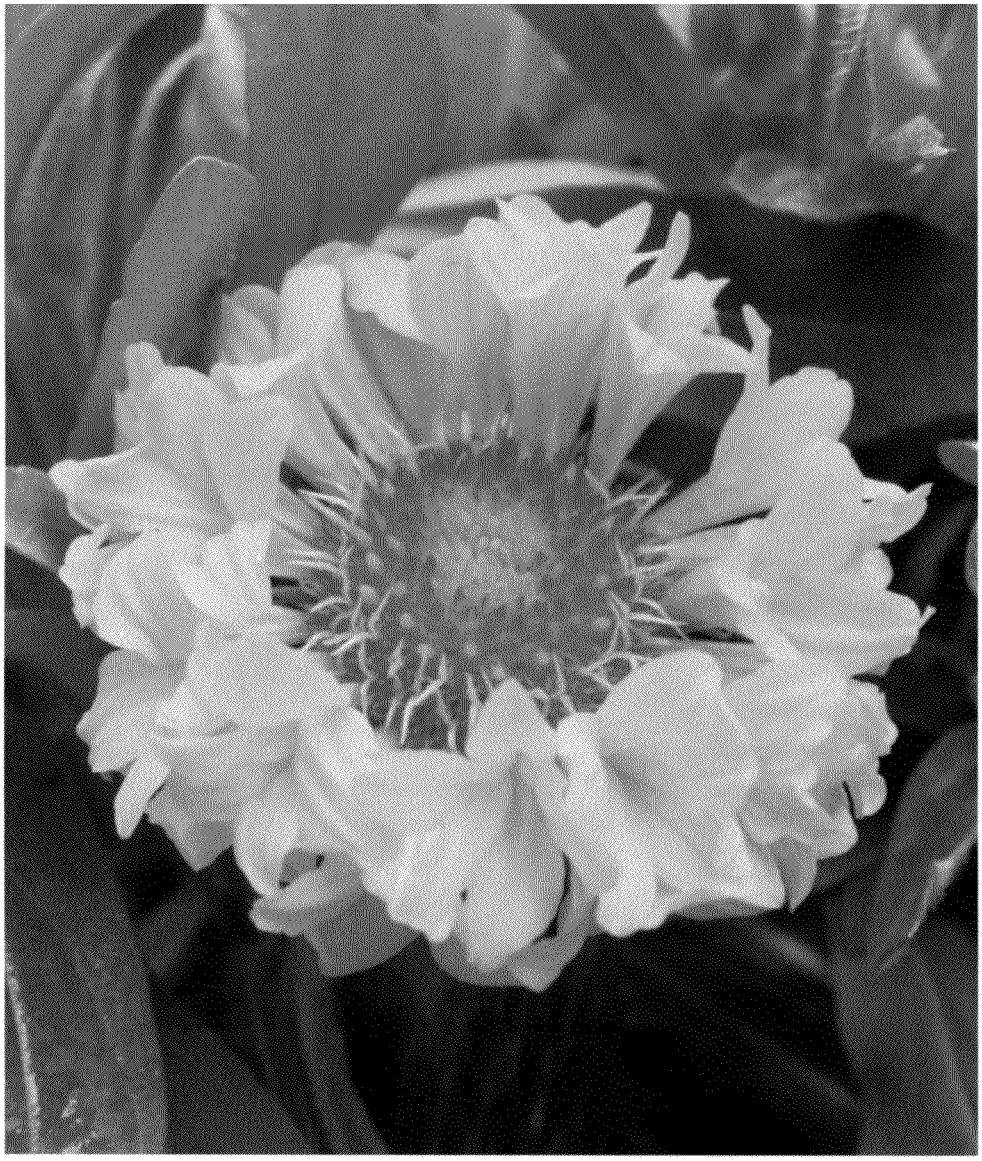

The photograph in FIG. 2 provides a close-up view of the inflorescence of 'Moxie'. The colors in the photographs are as close as possible with the digital photography and printing techniques utilized and the color codes in the detailed botanical description accurately describe the colors of the new *Gaillardia*.

DETAILED BOTANICAL DESCRIPTION

The detailed botanical data was collected from plants 6 months in age as grown outdoors in 6-inch containers in LaConner, Wash. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming season*.—Continuously from mid May to hard frost (end of October) in LaConner, Wash.

*Plant type*.—Herbaceous perennial.

*Plant habit*.—Compact and upright.

*Height and spread*.—12 to 18 inches in height and 18 to 24 inches in width.

*Cold hardiness*.—U.S.D.A. Zones 5.

*Diseases resistance*.—No susceptibility or resistance to diseases has been observed.

*Root description*.—Fibrous.

Growth and propagation:

*Propagation*.—Stem cuttings, root cuttings, and tissue culture.

*Growth rate*.—Moderately vigorous.

Stem description:

*Stem shape*.—Rounded.

*Stem aspect*.—Upright.

*Stem strength*.—Moderate.

*Stem color*.—144C.

*Stem surface*.—Pubescent.

*Lateral branch length*.—Average of 18 cm (excluding peduncles).

*Lateral branch diameter*.—Average of 4 mm.

*Quantity of lateral branches*.—About 8 per plant in a 6-inch container.

*Internode length*.—Average of 5 cm.

*Branching*.—Freely branched.

Foliage description:

*Leaf division*.—Simple.

*Leaf shape*.—Broadly oblanceolate to linear-oblong.

*Leaf base*.—Decurrent.

*Leaf apex*.—Broadly acute.

*Leaf margin*.—Entire.

*Leaf venation*.—Pinnate, 138D in color on upper and lower surface.

*Leaf attachment*.—Sessile.

*Leaf arrangement*.—Alternate.

*Leaf surface*.—Upper and lower surfaces; glabrous.

*Leaf color*.—Young foliage; upper surface 143A, lower surface 143B, mature foliage; upper surface, 143A, and lower surface 143B.

*Leaf size*.—Average of 7 cm in length and 3 cm in width.

Flower description:

General description:

*Inflorescence type*.—Terminal capitulum with many disc florets, one row of ray florets, and three rows of involucral bracts.

*Rate of flowering*.—Terminal inflorescence opens before lateral inflorescence.

*No. of days required for flowering response*.—An average of 8 weeks.

*Lastingness of inflorescence*.—About 3 weeks, persistent.

*Inflorescence aspect*.—Held upright.

*Fragrance*.—Moderately in strength, slightly sweet, chrysanthemum-like.

*Quantity of inflorescences*.—About 10 per plant in a 6-inch container.

*Inflorescence buds*.—About 10 mm in depth and 25 mm in diameter, flattened globular in shape, color 144C with center 144D.

*Inflorescence size*.—About 2 cm in depth and 7 cm in diameter, diameter of disk about 2.5 cm.

*Receptacle*.—Flattened globular in shape, about 4 mm in depth, 3 mm in diameter, 144C in color.

*Peduncle*.—Round in shape, upright, moderately strong, 142D in color, about 12 cm in length and 3 mm in diameter, surface slightly pubescent with soft hairs.

*Involucral bracts* (*phyllaries*).—Average of 30 per inflorescence, arranged in 3 rows, lanceolate to narrowly ovate in shape, narrowly acute apex, broadly cuneate base, margin entire and covered in villous hairs, upper surface dull and smooth and lower surface dull and densely covered with short hairs, 143B in color, about 25 mm in length and 15 mm in width.

Ray florets (capitulate):

*Number*.—Average of 18.

*Arrangement*.—Rotate, 1 whorl.

*Appearance*.—Upper surface smooth and dull, lower surface dull moderately covered with short hairs.

*Shape*.—Tubular (fluted), lower half fused into tube.

*Aspect*.—Held slightly upward.

*Size*.—Average of 3 cm in length and 20 mm in width.

*Petal apex*.—Three-lobed.

*Petal base*.—Tubular; flared at terminal.

*Petal margins*.—Entire.

*Petal texture*.—Upper surface smooth, lower surface moderately covered with short hairs.

*Petal color*.—Opening; inner surface 14A, outer surface 14A, fully open; outer surface 14A, inner surface 14A, senescing; upper surface 14B, lower surface 14C.

Disk florets (perfect):

*Quantity*.—Average of 60.

*Shape*.—Tubular with upper 30% free.

*Arrangement*.—Spiral concentric towards center of disc.

*Size*.—About 3 mm in length and 1 mm in width.

*Apex*.—Free, narrowly acute, entire margin.

*Base*.—Fused.

*Texture*.—Glabrous on inner and outer surfaces.

*Color*.—When opening upper and lower surface; tip 14A, mid-section 13C and base 144D, mature upper and lower surface; tip N25A, mid-section 14A and base 144D.

Reproductive organs:

*Presence*.—Disk flowers are perfect, ray flowers are carpellate.

*Gynoecium*.—1 pistil per disk and ray floret, 1.1 cm in length, stigma decurrent and 14C in color, style 2 mm in length and 14C in color, ovary 144C in color.

*Androecium*.—5 stamen per disk floret, filament 10 mm in length and 3D in color, anther linear in shape, about 2 mm in length and 3D in color with apex 203A, pollen; moderate in quantity and 14A in color.

*Fruit and seed*.—No fruits or seeds observed to date.

It is claimed:

1. A new and distinct variety of *Gaillardia* plant designated 'Moxie' as described and illustrated herein.

* * * * *